(12) United States Patent
Goldberg et al.

(10) Patent No.: US 11,636,949 B2
(45) Date of Patent: Apr. 25, 2023

(54) HYBRID KNOWLEDGE GRAPH FOR HEALTHCARE APPLICATIONS

(71) Applicants: Tal Goldberg, Even Yehuda (IL); Michal Tzuchman Katz, Tel Aviv (IL); Eitan Ron, Harutzim (IL)

(72) Inventors: Tal Goldberg, Even Yehuda (IL); Michal Tzuchman Katz, Tel Aviv (IL); Eitan Ron, Harutzim (IL)

(73) Assignee: KAHUN MEDICAL LTD., Givatayim (IL)

( * ) Notice: Subject to any disclaimer, the term of this patent is extended or adjusted under 35 U.S.C. 154(b) by 443 days.

(21) Appl. No.: 16/537,978

(22) Filed: Aug. 12, 2019

(65) Prior Publication Data

US 2020/0051694 A1 Feb. 13, 2020

Related U.S. Application Data

(60) Provisional application No. 62/717,552, filed on Aug. 10, 2018.

(51) Int. Cl.
| | |
|---|---|
| G16H 50/20 | (2018.01) |
| G16H 50/70 | (2018.01) |
| G06N 5/022 | (2023.01) |
| G16H 15/00 | (2018.01) |
| G16H 10/60 | (2018.01) |

(52) U.S. Cl.
CPC .............. *G16H 50/20* (2018.01); *G06N 5/022* (2013.01); *G16H 10/60* (2018.01); *G16H 15/00* (2018.01); *G16H 50/70* (2018.01)

(58) Field of Classification Search
CPC ........ G16H 50/20; G16H 10/60; G16H 15/00; G16H 50/70; G06N 5/022
See application file for complete search history.

(56) References Cited

U.S. PATENT DOCUMENTS

| | | | |
|---|---|---|---|
| 2007/0118399 A1* | 5/2007 | Avinash | G16H 40/20 705/2 |
| 2013/0291060 A1* | 10/2013 | Moore | G06F 16/83 726/1 |
| 2014/0257047 A1* | 9/2014 | Sillay | H04L 63/10 600/595 |
| 2015/0100341 A1* | 4/2015 | Pecora | G06F 16/285 705/2 |
| 2016/0140446 A1* | 5/2016 | Adderly | G06N 5/022 706/51 |

* cited by examiner

*Primary Examiner* — Jay M. Patel
(74) *Attorney, Agent, or Firm* — Fresh IP PLC

(57) ABSTRACT

A healthcare system, platform and methods for providing enhanced medical diagnostics and treatment are herein provided. The platform includes a healthcare knowledge graph database for storing a medical hybrid knowledge graph, the hybrid knowledge graph including healthcare data from one or more ontology-based knowledge graphs and clinical data from one on more sources; a data processing engine running a diagnostic algorithm, designed to process a patient condition data and to process a hybrid knowledge graph database, and select one or more pathways on the knowledge graph to generates one or more differential diagnoses for suspected disorders, which relate to the given patient condition; and a user interface to enable an end user to view results output by the data processing engine.

14 Claims, 12 Drawing Sheets

FIG. 1

| Source Disorder | Type of Rule | Rule Target | Probability | Strength of source | Link to source |
|---|---|---|---|---|---|
| Celiac disease (disorder) | ASSOCIATED CONDITION | Addison's disease (disorder) | 1-2 | 1 | https://www.ncbi.nlm.nih.gov/pmc/articles/PMC3496881/ |
| Celiac disease (disorder) | ASSOCIATED CONDITION | Alopecia areata (disorder) | 1-2 | 2 | https://www.ncbi.nlm.nih.gov/pmc/articles/PMC3496881/ |
| Celiac disease (disorder) | ASSOCIATED CONDITION | Diabetes mellitus type 1 (disorder) | 1-2 | 3 | https://www.ncbi.nlm.nih.gov/pmc/articles/PMC3496881/ |
| Celiac disease (disorder) | ASSOCIATED CONDITION | Migraine (disorder) | 2-5 | 4 | https://www.ncbi.nlm.nih.gov/pmc/articles/PMC3496881/ |
| Celiac disease (disorder) | ASSOCIATED CONDITION | Systemic lupus erythematosus (disorder) | 1-2 | 5 | https://www.ncbi.nlm.nih.gov/pmc/articles/PMC3496881/ |
| Celiac disease (disorder) | COMPLICATION | Bile acid malabsorption syndrome (disorder) | 2-5 | 5 | https://www.ncbi.nlm.nih.gov/pmc/articles/PMC3496881/ |
| Celiac disease (disorder) | COMPLICATION | Chronic diarrhea (disorder) | 10-20 | 1 | https://www.ncbi.nlm.nih.gov/pmc/articles/PMC3496881/ |
| Celiac disease (disorder) | COMPLICATION | Chronic liver disease (disorder) | 2-5 | 2 | https://www.ncbi.nlm.nih.gov/pmc/articles/PMC3496881/ |
| Celiac disease (disorder) | EXPOSURE | Gluten (substance) | 90-100 | 3 | https://www.ncbi.nlm.nih.gov/pmc/articles/PMC3496881/ |
| Celiac disease (disorder) | GENETIC MUTATIONS | HLA-DQ2 | 90-100 | 4 | https://www.ncbi.nlm.nih.gov/pmc/articles/PMC3496881/ |
| Celiac disease (disorder) | LABORATORY TESTS | Amylase [Enzymatic activity/volume] in Serum, Plasma or Blood:HIGH | 5-10 | 1 | https://www.ncbi.nlm.nih.gov/pmc/articles/PMC3496881/ |

FIG. 4

| Type of Feature | Feature | Likelihood with Celiac disease | Likelihood with Crohn's disease |
|---|---|---|---|
| SYMPTOM/COMPLAINT | Abdominal pain (finding) | 5-10 | |
| SYMPTOM/COMPLAINT | Abdominal pain (finding)# Chronic (qualifier value) | 90-100 | |
| COMPLICATION | Acute hepatitis (disorder) | 2-5 | |
| COMPLICATION | Acute intestinal obstruction (disorder) | 5-10 | |
| COMPLICATION | Acute upper gastrointestinal hemorrhage (disorder) | 2-5 | |
| ASSOCIATED CONDITION | Addison's disease (disorder) | 1-2 | |
| LABORATORY TESTS | Amylase [Enzymatic activity/volume] in Serum, Plasma or Blood:HIGH | 5-10 | |
| COMPLICATION | Anemia of chronic disorder (disorder) | | 5-10 |
| SIGNS | Ataxia (finding) | 1-2 | |
| ASSOCIATED CONDITION | Autoimmune hepatitis (disorder) | 1-2 | 5-10 |
| LABORATORY TESTS | Ceruloplasmin [Mass/volume] in Serum or Plasma:LOW | 2-5 | |
| COMPLICATION | Chronic diarrhea (disorder) | 10-20 | 5-10 |
| COMPLICATION | Chronic liver disease (disorder) | 2-5 | 2-5 |
| COMPLICATION | Constipation (disorder) | 5-10 | |
| COMPLICATION | Delayed puberty (disorder) | 2-5 | 5-10 |
| COMPLICATION | Depressive disorder (disorder) | 2-5 | |
| ASSOCIATED CONDITION | Diabetes mellitus type 1 (disorder) | 1-2 | |
| LABORATORY TESTS | Endomysium Ab [Units/volume] in Serum:HIGH | 90-95 | |
| COMPLICATION | Exacerbation of Crohn's disease of large intestine (disorder) | | 90-100 |
| COMPLICATION | Exocrine pancreatic insufficiency (disorder) | | 2-5 |
| SYMPTOM/COMPLAINT | Failure to gain weight (finding) | 5-10 | |
| COMPLICATION | Failure to thrive (disorder) | 60-70 | 30-40 |
| COMPLICATION | Iron deficiency anemia (disorder) | 5-10 | 5-10 |
| ASSOCIATED CONDITION | Migraine (disorder) | 2-5 | 2-5 |
| COMPLICATION | Osteopenia (disorder) | 2-5 | 5-10 |
| RISK FACTORS | Periods of life (qualifier value):ADULTHOOD | 30-40 | 40-50 |
| COMPLICATION | Vitamin D deficiency (disorder) | 2-5 | 10-20 |

FIG. 5

| Feature | Disease | Likelihood to present with disease |
|---|---|---|
| Failure to thrive (disorder) | Adrenal cortical hypofunction (disorder) | 20-30 |
| Failure to thrive (disorder) | Adrenocorticotropic hormone deficiency (disorder) | 30-40 |
| Failure to thrive (disorder) | Anemia (disorder) | 40-50 |
| Failure to thrive (disorder) | Atrial septal defect (disorder) | 5-10 |
| Ataxia (finding) | Celiac disease (disorder) | 1-2 |
| Failure to thrive (disorder) | Celiac disease (disorder) | 60-70 |
| Failure to thrive (disorder) | Crohn's disease (disorder) | 30-40 |
| Failure to thrive (disorder) | Chronic diarrhea (disorder) | 40-50 |
| Failure to thrive (disorder) | Chronic liver disease (disorder) | 20-30 |
| Failure to thrive (disorder) | Cystic fibrosis (disorder) | 30-40 |
| Ataxia (finding) | Degenerative disease of the central nervous system (disorder) | 70-80 |
| Failure to thrive (disorder) | Disorder of the urea cycle metabolism (disorder) | 60-70 |
| Failure to thrive (disorder) | Glucosylceramide beta-glucosidase deficiency (disorder) | 60-70 |
| Failure to thrive (disorder) | Glycogen storage disease type Ia (disorder) | 60-70 |
| Failure to thrive (disorder) | Malabsorption syndrome (disorder) | 20-30 |
| Failure to thrive (disorder) | Milk-induced pulmonary disease in infant (disorder) | 5-10 |
| Failure to thrive (disorder) | Mitochondrial cytopathy (disorder) | 60-70 |
| Failure to thrive (disorder) | Tyrosinemia (disorder) | 20-30 |
| Failure to thrive (disorder) | Tyrosinemia (disorder) | 60-70 |
| Ataxia (finding) | Tyrosinemia (disorder) | 5-10 |
| Failure to thrive (disorder) | Ventricular septal defect (disorder) | 10-20 |
| Ataxia (finding) | Wilson's disease (disorder) | 5-10 |

FIG. 8A

| EPIDEMIOLOGY | | | |
|---|---|---|---|
| Given | | Distribution | Breakdown By Gender |
| Ischemic heart disease (disorder) | | Population | Male (qualifier value) |
| | | | 65% |
| | | | Female (qualifier value) |
| | | | 35% |
| Publication Name | | | |
| Harrison's Principles of Internal Medicine, 20e | | | |
| Chapter | | | |
| 267: Ischemic Heart Disease | | | |
| Location (URL) | | | |
| https://accessmedicine.mhmedical.com/content.aspx?sectionid=192023647&bookid=2129&Resultclick=2#1168848746 | | | |
| | | | |
| Given | | Incidence of | Myocardial infarction (disorder) |
| Diabetes mellitus (disorder) | | | |
| | | | 46.5/10000/yr |
| | | | |
| Location (URL) | | | |
| http://www.ncbi.nlm.nih.gov/pubmed/24738687?dopt=Abstract | | | |
| | | | |
| Given | | Risk of | Myocardial infarction (disorder) |
| Atrial fibrillation (disorder) | | | |
| | | | 1.7x ↑ |
| | | | |
| Publication Name | | | |
| JAMA Intern Med 2014 Jan 1;174(1);107 | | | |
| Location (URL) | | | |
| https://www.ncbi.nlm.nih.gov/pubmed/24190540?dopt=Abstract | | | |

Figure 8B

PHYSICAL SIGNS / SYMPTOMS

| Given | | | |
|---|---|---|---|
| Ischemic heart disease (disorder) | Outcome of | Dyspnea (finding) | |
| | | Overall | 70-80% |
| | | Breakdown By Character | |
| | | Intermittent (qualifier value) | |
| | | | 80-90% |

Publication Name
Harrison's Principles of Internal Medicine, 20e

Chapter 33: Dyspnea
Location (URL)
https://accessmedicine.mhmedical.com/content.aspx?bookid=2129&sectionid=192012428

---

IMAGING

| Given | | | |
|---|---|---|---|
| Ischemic heart disease (disorder) | Outcome of | ST segment depression (finding) | |
| | | Procedure Electrocardiographic | |
| | | | 40-50% |

Publication Name
Harrison's Principles of Internal Medicine, 20e
Chapter
267: Ischemic Heart Disease
Location (URL)
https://accessmedicine.mhmedical.com/content.aspx?sectionid=192028847&bookid=2129&Resultclick=2#1160046748

---

COMPLICATIONS

| Given | | | |
|---|---|---|---|
| Given | Outcome of | Ventricular premature beats (disorder) | |
| Ischemic heart disease (disorder) | | | |
| | | | 40-50% |

Publication Name
Harrison's Principles of Internal Medicine, 20e
Chapter
267: Ischemic Heart Disease
Location (URL)
https://accessmedicine.mhmedical.com/content.aspx?sectionid=192028847&bookid=2129&Resultclick=2#1160046748

HYBRID KNOWLEDGE GRAPH FOR HEALTHCARE APPLICATIONS

CROSS REFERENCE TO RELATED APPLICATIONS

This application claims priority from U.S. Provisional Patent Application No. 62/717,552, filed 10 Aug. 2018, entitled "A METHOD AND A SYSTEM TO GENERATE A MACHINE-READABLE MEDICAL KNOWLEDGE BASE AND UTILIZE IT FOR HEALTHCARE APPLICATIONS", which is incorporated in its entirety herein by reference.

FIELD OF THE INVENTION

The present invention relates in general to methods and devices useful in generating a structured, machine-readable version of medical knowledge and using it for healthcare applications.

BACKGROUND OF THE INVENTION

For generations, the general approach of the medical community for sharing medical knowledge has been built around publishing textbooks and peer-reviewed articles in medical journals. Therefore, existing medical databases are typically unstructured textual repositories for such articles. E.g. PubMed—by the US National Library of Medicine—holds over 27 million articles. MD's and researchers use such articles both as part of their never-ending educational process and when in specific need to diagnose and treat individual patients.

The amount of medical information is growing exponentially with thousands of new articles published every month for each specific medical specialty. Medical professionals are in constant struggle to stay updated. When in need for information, their preferred option is to do a literature search and read through relevant sources which address the case being investigated. Unfortunately, most times in medical practice, physicians just don't have the time to do such a literature search and are guided by their experience and memory of medical knowledge they have once learned. This often results in cases of diagnostic errors, unnecessary tests and higher cost of medical care.

In the last ~20 years, several coding and nomenclature systems have emerged in the field of medicine, with a goal to create global standards for health terms in order to fuel worldwide standardization of medical data collection and sharing and enable the development of standard medical software, especially in the area of electronic health records (EHR systems). ICD (International classification of diseases) and SNOMED are examples for two such systems. While ICD is a coding system, SNOMED is an example for an encompassing Ontology covering hundreds of thousands of medical terms arranged as an ontology. This development was essential for driving the development of the HER industry and promote its use in clinical environment.

However, such Ontologies have generally been restricted to health terms and their semantic relations. Clinical relations were out of scope for such Ontologies. The existing ontology, for example, captures knowledge about body parts and their relations, for example, defining that a hand is a body organ which is part of a body, and that a finger is part of a hand. It also holds sets of relations and qualifiers that support detailed description of medical concepts, as well as names of findings and disorders that can be grouped in families. But such Ontologies do not deal with clinical relations such as the likelihood of having a chest pain when experiencing MI. In other words, the ontology describes chest pain and MI separately, but it does not describe the relation between the two as would appear in a medical article dealing with MI. For this reason, Ontologies such as SNOMED are generally not known or used by medical professionals, and are typically used by Health administrators, researchers, developers of EHR systems, etc.

Furthermore, when physicians run into complex cases they typically use a decision-making process known as clinical reasoning. To do so, they generally analytically generate, refine and discard diagnostic hypotheses while examining and testing the patient. This process, which may occur in the minds of trained physicians, relies heavily both on their clinical memory and their ability to apply statistical thinking taking into account elements such as disease incidence rates, specificity and sensitivity of tests and strengths of associations between findings and diagnosis hypothesis. So far, one of the main inhibitors for using computers to help physicians in this analytic task was the lack of comprehensive clinical data available in a structured, machine-readable format.

It would be highly advantageous to have a system or method that could enable a computerized means that integrates medical term ontologies as described above along with operational databases, such as costs of lab tests, medication side effects and traditional medical knowledge, to improve healthcare, cut costs of care, and reduce the number of unnecessary tests and diagnostic errors.

SUMMARY OF THE INVENTION

There is provided, in accordance with an embodiment of the present invention, a platform, system, and method to generate a hybrid knowledge graph based on clinical knowledge together with other ontology based knowledge graphs, adapted for usage in healthcare applications, comprising: an associative medical knowledge base; a crowdsourcing and community-based editing module; healthcare applications such as a patient management application running on an end user device; or a medical features data retrieval and comparison application, connected to the associated medical knowledge base.

In some embodiments, the patient management application runs a file with instructions to execute commands to enable execution of one or more healthcare applications.

There is provided, in accordance with an embodiment of the present invention, a platform for generating a machine-readable medical knowledge base for healthcare applications, including: an associative medical knowledge base; a crowdsourcing and community-based editing, moderation and validation modules; and one or more healthcare applications running on an end user device.

In some embodiments, the healthcare application is designed to manage a patient through a diagnosis process.

In some embodiments, the healthcare application provides access to the associative medical knowledge base for answering clinical questions and browsing through its associative content.

In some embodiments, the healthcare application runs a file with instructions to execute commands to manage a patient through a diagnosis process.

In some embodiments, the healthcare application provides access to the associative medical knowledge base for answering clinical questions and browsing through its associative content.

According to some embodiments, a method is provided for generating a machine-readable medical knowledge base for healthcare applications, comprising elements described herein.

There is provided, in accordance with an embodiment of the present invention, a healthcare platform for generating medical diagnostics, comprising: a healthcare knowledge graph database for storing a medical hybrid knowledge graph, the hybrid knowledge graph including healthcare data from one or more ontology-based knowledge graphs and clinical data from one on more sources; a data processing engine running a diagnostic algorithm, designed to process a patient condition data and to process a hybrid knowledge graph database, and select one or more pathways on the knowledge graph to generates one or more differential diagnoses for suspected disorders, which relate to the given patient condition; and a user interface to enable an end user to view results output by the data processing engine.

In some embodiments, the hybrid knowledge base further includes a healthcare treatment algorithm, designed to run on one more healthcare treatment data sources, to generate a plurality of treatment pathways relating to a patient condition.

In some embodiments, the hybrid knowledge base further includes a healthcare clinical data translation module, for adapting published healthcare content into machine readable knowledge base for usage in healthcare applications.

In some embodiments, the hybrid knowledge base further includes a one or more data curation modules selected from the group consisting of: a crowdsourcing module, a community-based editing module, a data moderation module, a data validation module, and a data scoring module.

In some embodiments, the hybrid knowledge base further includes a healthcare application that runs a file with instructions to execute commands to manage a patient through one or more processes including a diagnosis process, a treatment process, a consulting process, a payment process, a citation research process, a regression testing process, and a lab testing process.

In some embodiments, the hybrid knowledge base further includes a module to provide next step suggestions, to filter the differential diagnoses.

In some embodiments, the hybrid knowledge base further includes a reasoning path provided to back up each generated diagnosis, the reasoning path being inferred from the knowledge graph.

In some embodiments, the hybrid knowledge base further includes reasoning paths supported by original citations, the citations optionally containing clinical rules used to generate the relevant diagnosis.

In some embodiments, the hybrid knowledge base further includes a rule to require the citations to be provided with ratings which include a score of the citation provided.

In some embodiments, the diagnostics algorithm is designed to provide priority to citations with higher ratings.

In some embodiments, the platform further includes a data validation module to validate curated data by running multiple patient conditions, along with known diagnoses.

In some embodiments, the hybrid knowledge base is further designed to include newly curated data that may result in a diagnosis which differs from an expected diagnosis, and wherein the platform may run a rule on the hybrid knowledge base to apply further moderation for the newly curated data.

There is provided, in accordance with an embodiment of the present invention, a medical diagnostic method, comprising: running a diagnostic algorithm designed to process patient condition data and to process a hybrid knowledge graph database, and select one or more pathways on the knowledge graph to generate one or more differential diagnoses for a suspected disorder, which relates to the given patient condition(s); and presenting the differential diagnosis on an end user interface, wherein the hybrid knowledge graph includes a healthcare terminology knowledge graph and healthcare clinical data knowledge graph.

In some embodiments, the medical diagnostic method further includes running a healthcare treatment algorithm designed to process patient condition data and to process a hybrid knowledge graph database, and select one or more pathways on the knowledge graph to generate one or more treatment pathways for a suspected disorder, which relates to the given patient condition(s).

In some embodiments, the medical diagnostic method further includes running a diagnostic algorithm on a hybrid knowledge graph that includes data integrated from one or more healthcare treatment knowledge graphs.

There is provided, in accordance with an embodiment of the present invention, a system for managing medical treatments, including: a healthcare knowledge graph database for storing a medical hybrid knowledge graph, the hybrid knowledge graph including healthcare data from one or more ontology-based knowledge graphs and clinical data from one on more sources; a data processing engine running a treatment pathway algorithm, designed to process a patient condition data and to process a hybrid knowledge graph database, and select one or more pathways on the knowledge graph to generates one or more treatment pathways for suspected disorders that relate to the given patient condition.

In some embodiments, the hybrid knowledge base further includes a healthcare treatment algorithm, designed to run on one more healthcare treatment data sources, to generate a plurality of treatment pathways relating to a patient condition.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein:

FIG. 1 is a table showing a sample of knowledge base rules for Celiac disease, according to some embodiments;

FIG. 4 is a table showing a sample result of a Medical Features Data Retrieval and Comparison, illustrating a feature by feature comparison for two selected diseases (CROHN's and CELIAC), according to some embodiments; and FIG. 5 is a table showing a sample result of a Medical Features Data Retrieval and Comparison, illustrating a list of diseases with likelihood to present given features (Failure to thrive & ataxia), according to some embodiments.

FIGS. 8A and 8B show examples of interfaces that describes clinical rules relating to Myocardial infarction as entered within a content editor of the present invention, according to some embodiments;

DETAILED DESCRIPTION OF THE INVENTION

Figure 2:
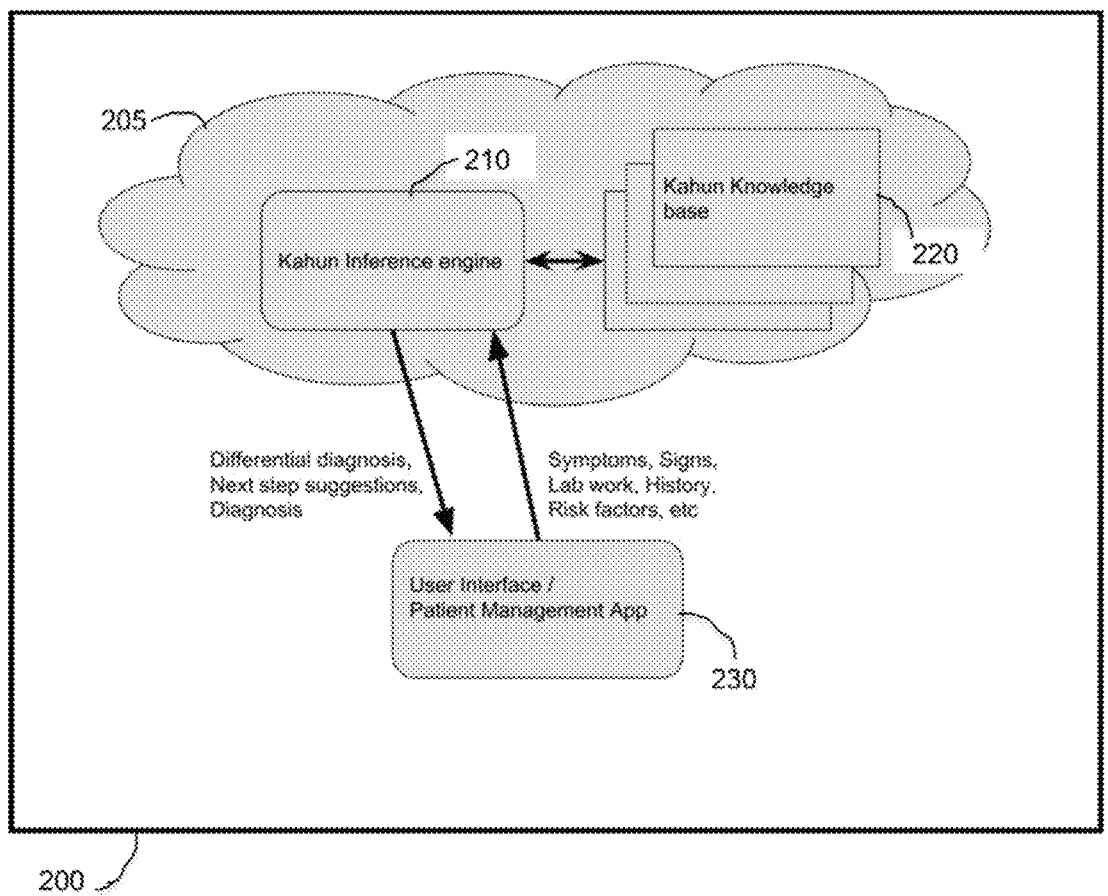
FIG. 2 shows a schematic view of a system for providing a structured knowledge base and related patient management applications, according to some embodiments.

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

The word "healthcare" as used herein may encompass the organized provision of medical care to individuals or a community, efforts made to maintain or restore physical, mental, or emotional well-being, and the maintenance or improvement of health via the prevention, diagnosis, and treatment of disease, illness, injury, and other physical and mental impairments in people. The term "knowledge graph" as used herein may encompass a model of a knowledge domain created by subject-matter experts Of course, other definitions or interpretation may be used to broadly describe these terms.

Non-limiting embodiments of the present invention include a platform, system, and method to generate a machine-readable medical knowledge base for healthcare applications, comprising: an associative medical knowledge base; a crowdsourcing and community-based editing module; a patient management application running on an end user device; and a medical features data retrieval and comparison application, connected to the associated medical knowledge base.

A method and system are herein provided that enable the translation of medical knowledge from multiple sources (e.g., books, articles, publications, personal knowledge etc.), into a hybrid knowledge graph which integrates clinical knowledge along with other ontology based knowledge graphs, such as SNOMED, LOINC or other types of medical databases (e.g., including costs and risks of lab and imaging tests, medicine's side-effects, disease prevalence and incidence rates, etc.). In this way, the various data sources relating to multiple medical conditions are reflected in a hybrid healthcare knowledge graph, optionally reviewed and verified by a crowdsourcing platform.

According to some embodiments, an Associative Medical Knowledge Base is provided, based on a new type of a structured medical knowledge base, which organizes medical data in an associative, machine-readable format. The knowledge base holds a probabilistic association between various disease and disorder features such as: Risk factors, Associated conditions, Time course, Clinical manifestations, Laboratory findings, Imaging, Complications, Management, treatment, etc. In some examples, a chapter in a medical textbook or an article describing a certain disease may be translated into a number of such associations indicating the probability which links each feature with the disease. The knowledge base may also hold data such as the monetary cost or risk of laboratory, imaging tests or other procedures.

According to some embodiments, the structured associative medical knowledge base is provided, that integrates two or more separate knowledge graphs. In one example, a first knowledge graph is derived from a healthcare Ontology which includes a large vocabulary of medical concepts. (e.g., SNOMED). Such an ontology is to include descriptions of non-clinical relations between medical concepts such as disorders, findings, body parts, etc. A second knowledge graph is derived from a different source such as an ontology dedicated to laboratory tests and procedures (e.g., LOINC). A third knowledge graph is created or generated by medical experts or healthcare professionals, who research medical publications to build a clinical probability graph that describes clinical statistical information that links medical concepts that are described in the Ontological graphs. For example, such medical experts may use a template-based editor which is designed to provide the templates and flexibility required for translating, processing and/or filtering complex medical concepts and relations, in a way that can be read by and understood by the system and platform described herein. In this way, the generated Associative Medical Knowledge Base is effectively a new hybrid knowledge graph which provides a model for presenting and describing medical knowledge as it appears in the medical literature.

Data is derived from evidence-based or other sources. Each such association within the knowledge base has a source such as textbook, article etc. The knowledge base will contain the source along ranking to indicate its relative strength. E.g. if a certain association is based on an article published by a reputable expert in one of the top medical journals it will carry a higher score than an association which is based on a less known source. An association supported by multiple research would also get a higher score.

In a preferred embodiment, a community of experts uses an editor to enters medical data which describes associations between diseases and other clinical features into a medical knowledge base. The data may also include items such as cost of laboratory and imaging tests or the level of risk and pain associated with such tests. The system may support storing and displaying the details (name of publication, link, etc.) for the sources of the associations it holds.

In a specific embodiment the Associative Medical Knowledge Base will include data which represents the strength of data sources. Such data will be either entered directly by the community experts or calculated using dedicated code to assign strength weights based on several factors e.g. strength of evidence and published research, academic strength of contributor, number of contributions by such member, her internal ranking, etc.

In a specific embodiment the Associative Medical Knowledge Base will include functionality for community moderation as well as a dedicated automated mechanism to validate data entered by community members as described below in the community platform section.

Reference is now made to FIG. 1, which is a table showing a sample of knowledge base rules for Celiac disease, according to some embodiments. As can be seen, FIG. 1 illustrates several sample rules which pertain to a specific gastrointestinal disease. These rules are provided only for illustration purposes and are not necessarily clinically accurate.

One skilled in the art will appreciate that, without departing from the spirit of the invention, the Knowledge Base part of the invention may be implemented in several different ways, in a single or multiple locations, cloud based or not, and include various suitable features for security, administration, etc.

FIG. 2 shows a schematic view of a system for providing structured knowledge base and patient management applications, according to some embodiments. As can be seen, patient management system or platform 200 includes a cloud-based inference engine 210, communicatively coupled to a knowledge base 220, and a patient management App. 230.

In some embodiments, the Patient Management App 230 is designed to assist physicians in managing a patient through the diagnosis process. The app offers physicians a way to make an updated, evidence-based clinical decision related to the evaluation and management of a patient throughout the diagnosis process.

The app uses the associations within the structured medical database to evaluate all the data available for a certain patient and recommend the next step for evaluation. Upon a list of given history, symptoms, signs and other clinical features the app generates a list of suspected diseases and complications. Then, the app suggests the next best step to narrow down that list by ruling in some diseases or ruling out other high-risk diseases. The App algorithm takes into consideration the strength of the various associations as indicated in the knowledge base as well as data such as the cost or pain and time it takes to get required lab tests, imaging or other diagnostic procedures.

By combining a constantly updated differential diagnosis list along with patient-tailored best next step recommendation, the app essentially creates on the fly a protocol for managing the diagnosis process for each patient.

In some embodiments, App algorithms are used that are based on mathematical inference computations adapted to handle the large number of associations between the various clinical features. One skilled in the art will appreciate that there are several alternative ways to implement such an inference engine without departing from the spirit of the invention.

Figure 3:
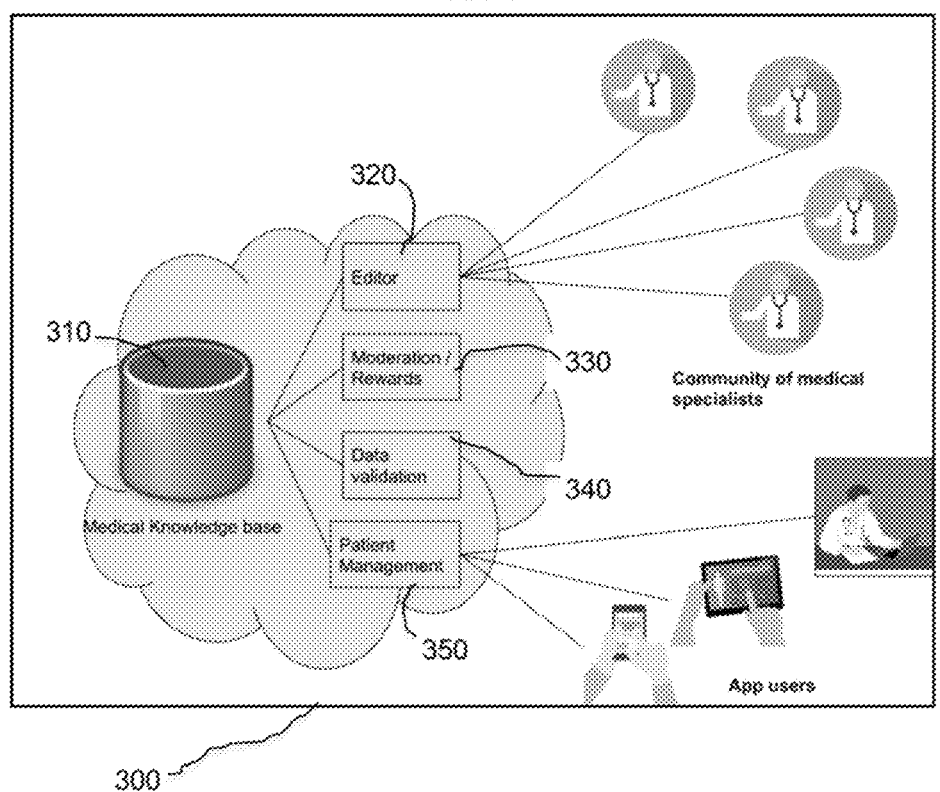
FIG. 3 is a schematic view of cloud based medical knowledge base modules, with community contributors and app users according to some embodiments.

FIG. 3 is a schematic view of the cloud based medical knowledgebase and its modules, in communication with community contributors and app users, according to some embodiments. As can be seen, platform 300 may include a Medical knowledgebase 310, which is curated and maintained by a community of medical specialists. The amount of available medical knowledge and its growth rate require a coordinated effort by a large group of contributors. The Knowledgebase 310 may be updated on an ongoing basis.

Community platform 300 further includes several modules: Editor 320—an interface in the form of a mobile app or web interface for data entry by community members; Moderation and rewards module 330—dedicated software code to manage content added by community members and provide rewards and acknowledgement for data contribution. The code will support moderation functionality to enable accepting or rejecting new content; Data validation module 340—to automatically validate new data entries in order to make sure they do not contain erroneous data. Data validation will be achieved by automated use of a dedicated code which would work in a fashion similar to the patient management application described below. The validation code would run a large number of cases with expected known results, new data which would cause a change in diagnosis for such cases would create an alert to be handled by a community moderator; and Patient Management module 350, which may be used to manage a patient through the diagnosis process.

Some of the above described modules may be implemented using one or more front-end and server-side techniques, software environments and development languages.

In one preferred embodiment the application utilizes the above mentioned Associative Medical Knowledge Base to create a differential diagnosis list based on inputs entered for a specific patient (e.g. demographics, history, symptoms, signs, lab results, etc.) The application uses the inputs and their corresponding associations within the knowledge base to run a mathematical inference algorithm that finds the most likely explanation for the patient's condition.

In one specific embodiment, the application can rank likely differential diagnosis results by their probabilistic score. The application may also recommend the best next steps to manage the patient and continue the diagnosis In one preferred embodiment the application can take into account both test or procedure costs, related pain and risk and its value in advancing the diagnosis process. E.g. it may recommend test A over test B due to reasons such as: Test B is more expensive, more dangerous or more painful, A positive or negative answer for test A would increase the probability of suspected diagnosis, etc.

In one preferred embodiment the app understands the concept of complications and its relation to diseases in the same way physicians do and can connect clinical manifestations to its originating diseases via a path that includes problem lists and complications of such diseases. E.g. A liver disease may cause a complication which in turn causes the patient to present with jaundice. The application would know to track the jaundice back to its complication and to the originating liver disorder.

In some embodiments the app can show a "path to decision". I.e. the clinical reasoning path of associations which were used in order to make a certain diagnosis or recommend a next step including details or links to original medical textbook or academic paper sources. The app may also display a "strength score" illustrating the sources' reliability.

In some embodiments, as can be seen with reference to FIGS. 4 and 5, the Medical Features Data Retrieval and Comparison is designed to provide clinical answers for various questions. We believe it offers great value for medical students, researchers and practicing physicians. This app is designed to display disease features which are stored in the associative medical database described above. E.g. for providing all the clinical manifestations related to a certain disease along with their likelihood to present, or all the diseases that share a combination of one or more lab test results. It can also be used to compare and contrast all the features which are related to two or more diseases either directly or via other complications. One skilled in the art will appreciate that the app is an interface for query-based interaction with the knowledge base and can be implemented in one of several different technologies.

In a preferred embodiment a mobile app or web interface enables browsing the above mentioned Associative Medical Knowledge Base and enables accessing any of the data elements within the Associative Medical Knowledge Base along with its associations with other features.

FIG. 4 is a table showing a sample of a Medical Features Data Retrieval and Comparison, illustrating a feature by feature comparison for two selected diseases (CROHN's and CELIAC), according to some embodiments. The example shown provides an example for data query from the Associative Medical Knowledge Base which provides an answer for questions such as "How do CROHN's and CELLIAC compare", and other questions.

In a specific embodiment, as can be seen with reference to FIG. 4, the application can be used for comparing two or more disease using a table format to compare the two or more diseases feature by feature.

FIG. 5 is a table showing a sample of a Medical Features Data Retrieval and Comparison, illustrating a list of diseases with likelihood to present given features (Failure to thrive & ataxia), according to some embodiments. The example shown provides an example for a data query which provides an answer for a question like: "what are all the diseases which could present with a "Failure to Thrive" and what is the likelihood of the presentation.

In another specific embodiment, as can be seen with reference to FIG. 5, the application can be used to present all the diseases which share the same set of features.

In a specific embodiment the mobile app or web interface may show any depth of associations. (e.g. directly related symptoms of a certain disease, or symptoms related via one or more complications). It may also show along with every query result its information source and its strength as described above.

According to some embodiments, a hybrid knowledge graph is provided, that includes two or more knowledge healthcare related graphs. One graph is typically an ontology of concepts, a second graph is typically a description of clinical relations between the concepts described in medical literature. Additional or other graphs may also be integrated into the hybrid knowledge graph. The hybrid knowledge graph is designed to present or describe content from a large variety of medical texts, data, presentations or other publications, in a standardized, repeatable manner, based on the usage of knowledge graph templates which support the different types of relations described in the medical data. For example, the knowledge graph is designed to describe relations, such as causality, etiology, prevalence, risk factors etc., between medical or healthcare concepts. In some cases, automated data processing may be used to sort and filter medical content, whereas in other cases, due to the complexity of such medical content, human experts may be required to understand the text and use pre-defined templates to process the data and define the clinical relations.

Figure 6:
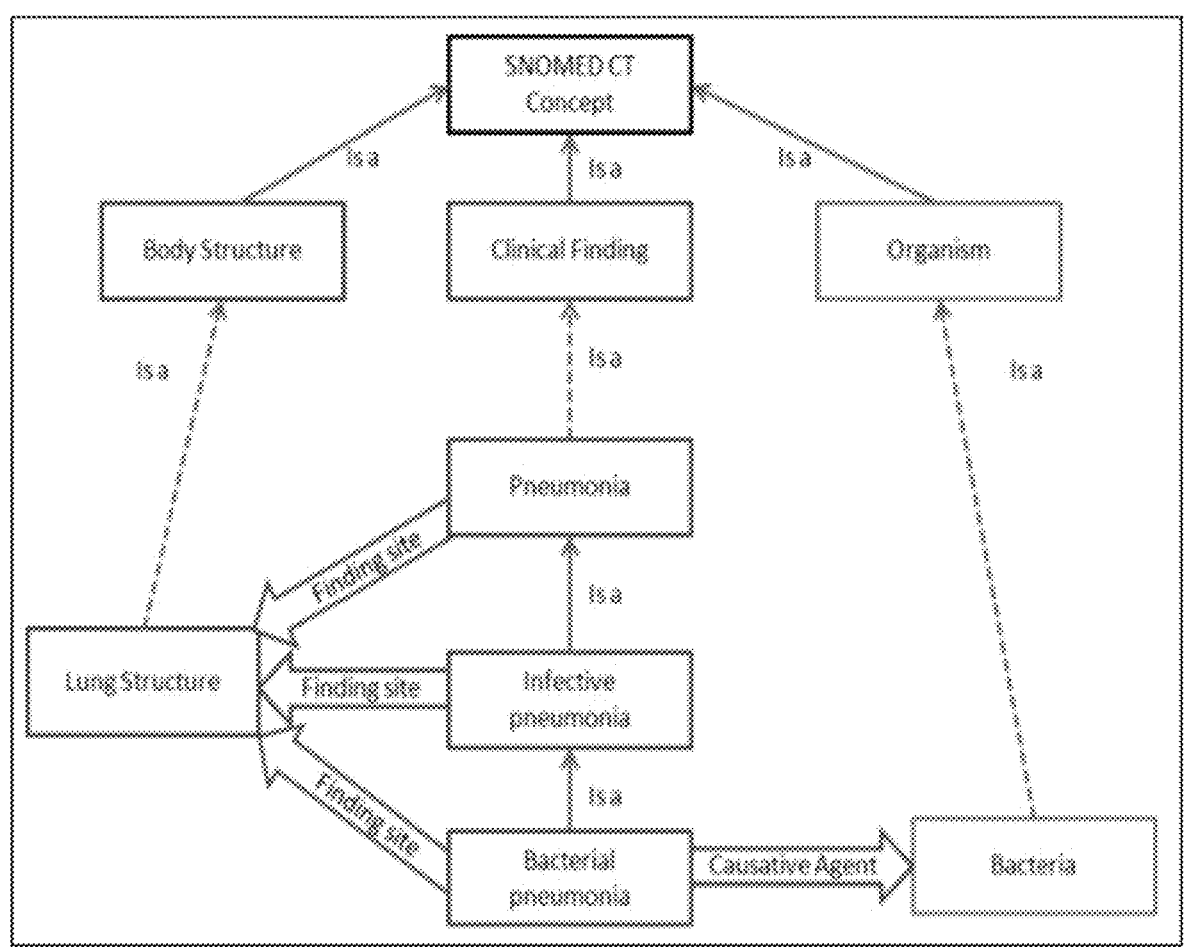
FIG. 6 shows an example of a description of a SNOMED concept tree, as may be used in some embodiments.

Reference is now made to FIG. 6, which shows an example of a description of a SNOMED concept tree, described in a knowledge graph format. As can be seen, different concepts and their relations are shown, however there are no clinical relations between concepts shown in this graph.

Figure 7:
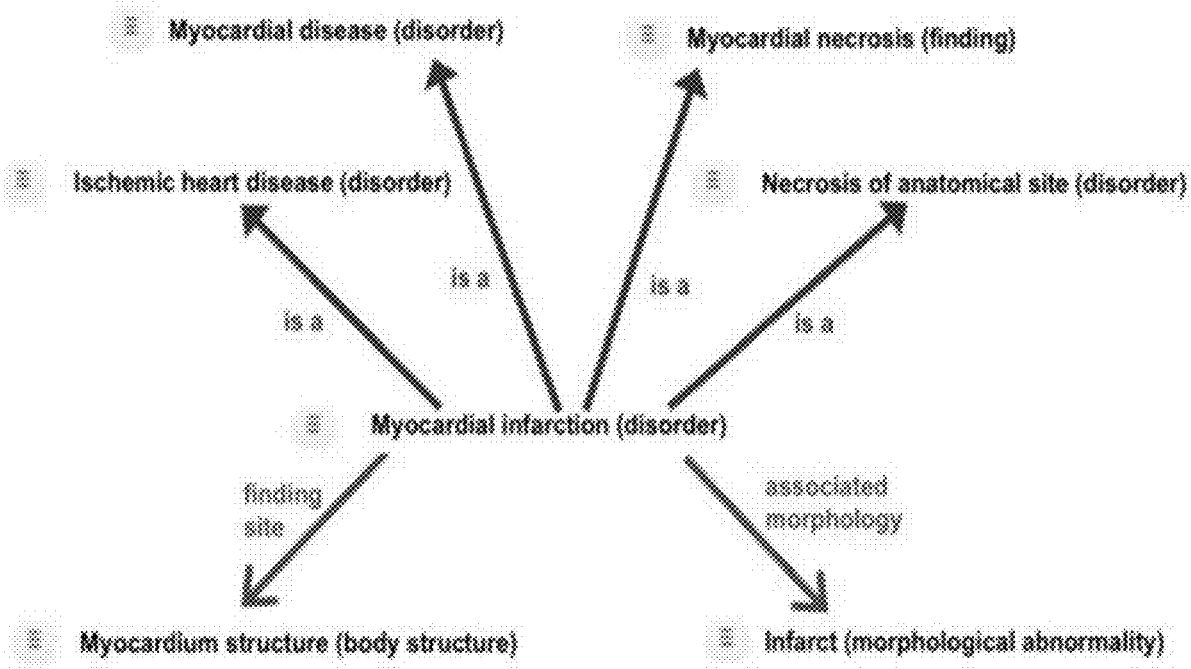
FIG. 7 shows an example of a sub SNOMED graph describing semantic relations around Myocardial infarction, according to some embodiments.

Reference is now made to FIG. 7, which shows an example of a sub SNOMED graph describing semantic relations around Myocardial infarction. As can be seen, semantic relations are shown, however there are no clinical relations between concepts shown in this graph.

Reference is now made to FIGS. 8A and 8B, which show examples of interfaces that describe clinical rules relating to Myocardial infarction as entered within the content editor of the present invention, according to some embodiments. As can be seen, a model is provided herein which enables capturing the full textual description of the relations between the medical concepts. The figures show samples of different templates used by the model for capturing citations of rules between medical concepts as they appear in medical literature.

Figure 9:
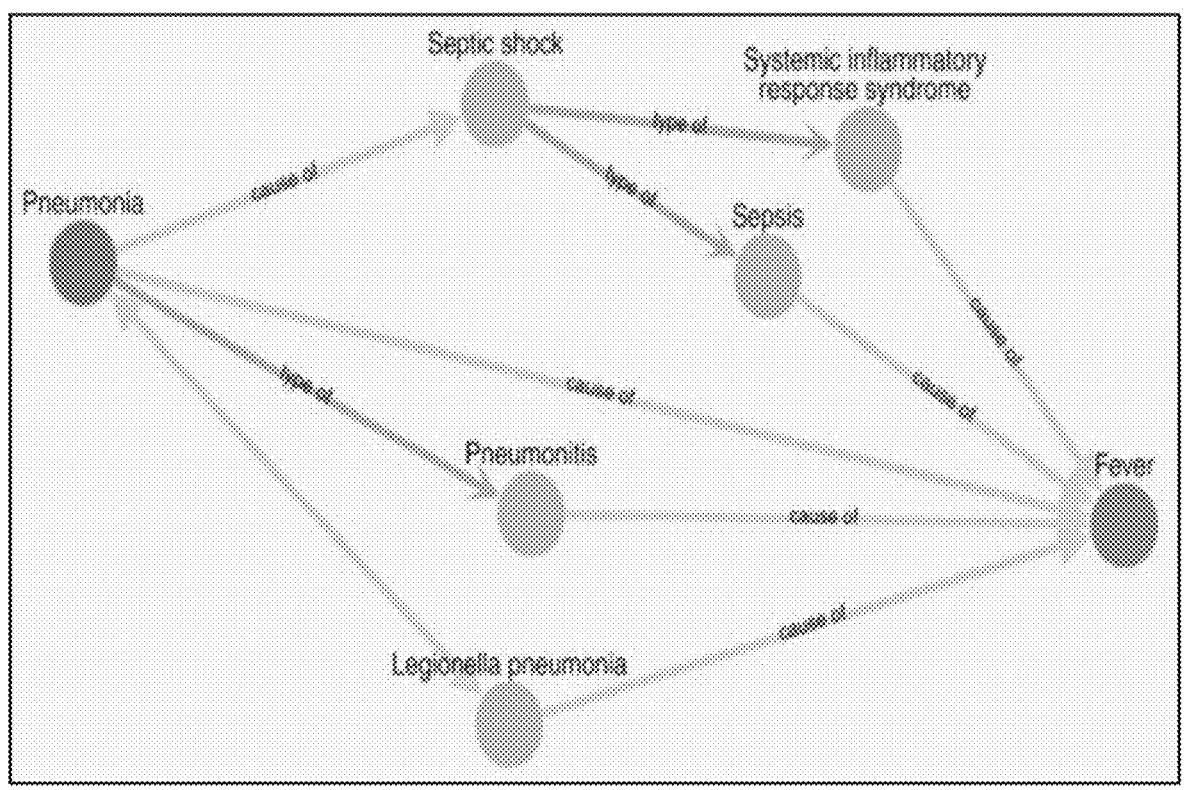
FIG. 9 shows an example of a hybrid graph showing clinical relations connecting Pneumonia and Fever, according to some embodiments.

Reference is now made to FIG. 9, which shows an example of a hybrid graph showing clinical relations connecting Pneumonia and Fever. As can be seen, darker arrows represent SNOMED "type-of" relations. Lighter arrows reflect clinical relations taken from medical literature. In this graph, an arrow represents a causal relationship (the numeric value of such relationship is not shown on the graph), whereas a double-sided arrow represents a clinical association between two concepts, according to some embodiments.

Figure 10:
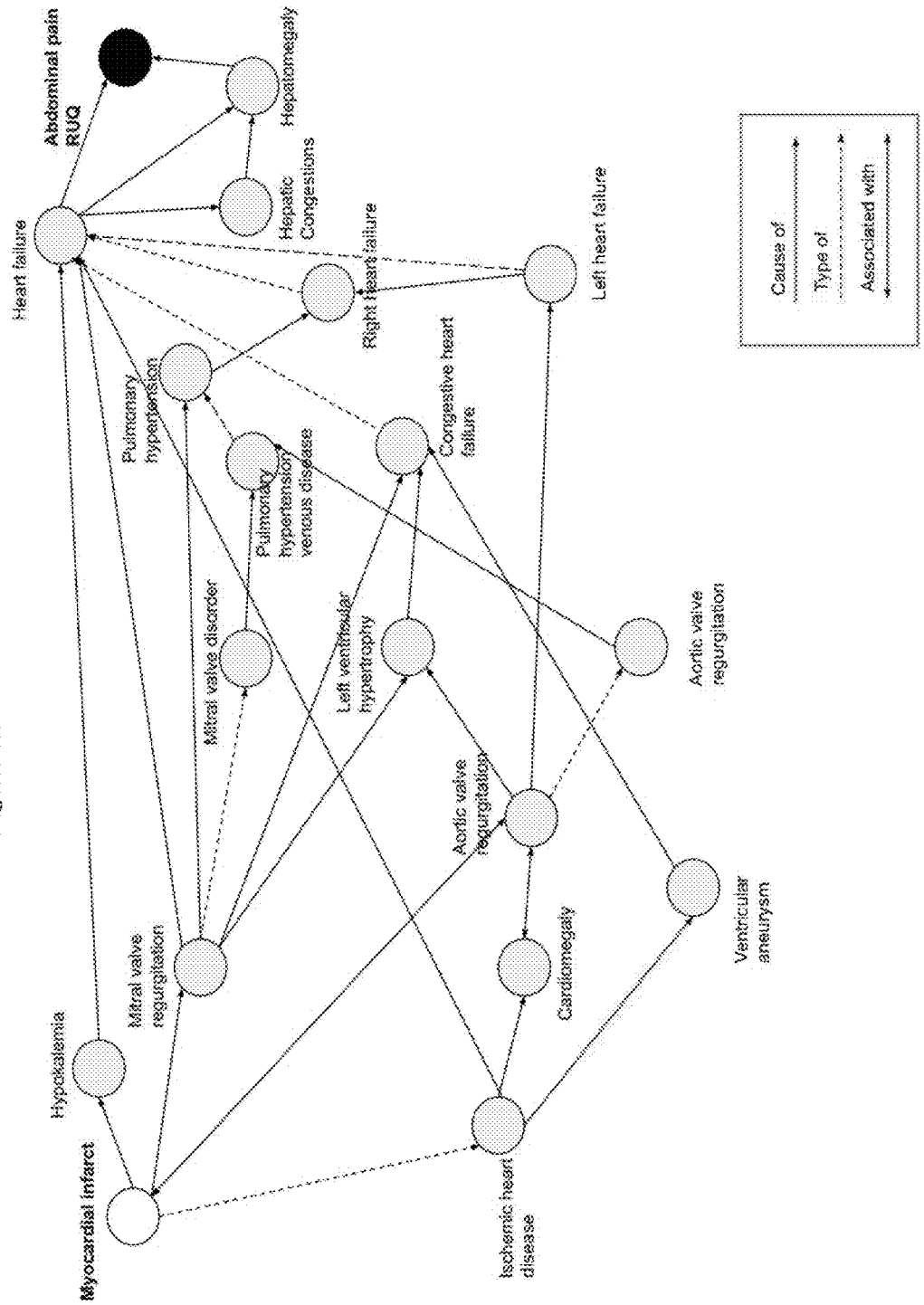
FIG. 10 shows an example of a hybrid graph showing connections between Myocardial infarction and abdominal pain, according to some embodiments.

Reference is now made to FIG. 10, which shows an example of a hybrid graph showing connections between Myocardial infarction and abdominal pain. As can be seen, darker arrows represent SNOMED "type-of" relations. Lighter arrows reflect clinical relations taken from medical literature. A single direction arrow represents a cause, whereas a double-sided arrow represents a clinical association between two concepts, according to some embodiments. It is noted that the complexity of such sub-knowledge graph depends on the number and length of paths connecting an originating disease and a symptom.

Figure 11:
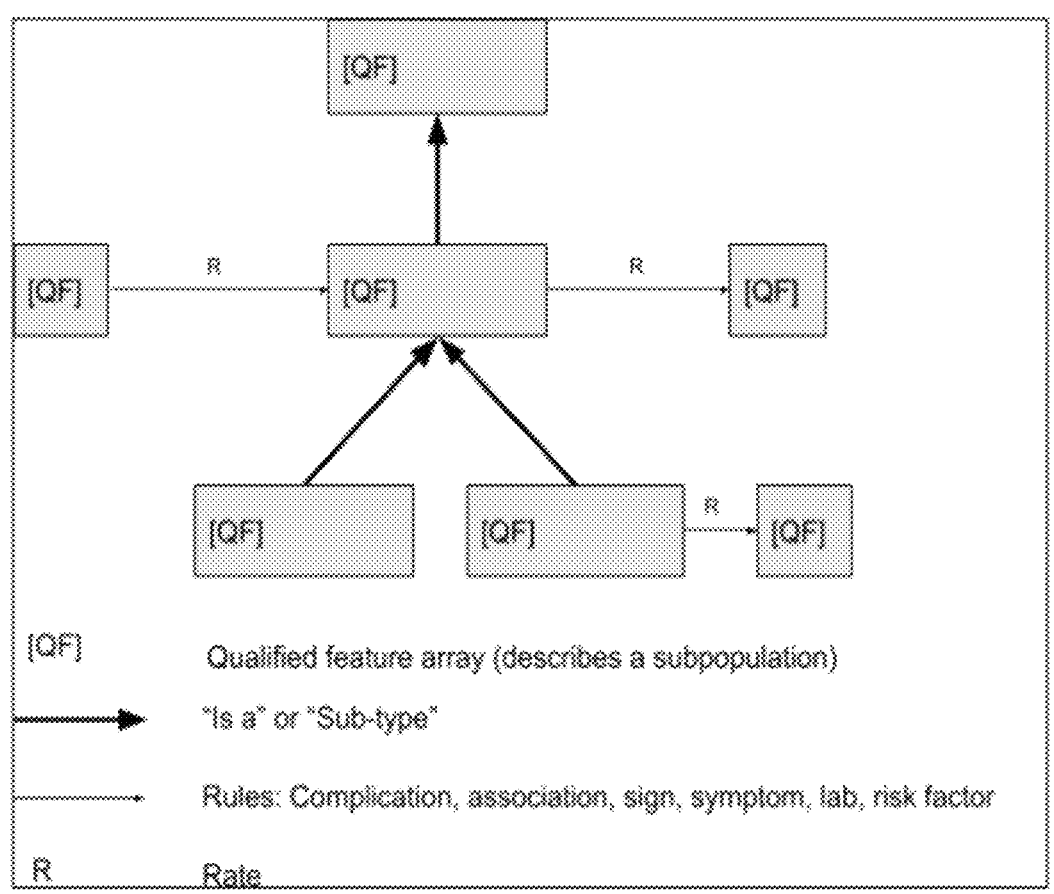
FIG. 11 shows an example of a model describing probabilistic relationships between medical concepts as they appear in medical texts, according to some embodiments.

According to some embodiments, a clinical knowledge base is combined with ontology knowledge graph, to create a data model that supports the complexities of accrued medical knowledge, and combines both a selected ontology graph and a selected clinical graph. As can be seen with reference to FIG. 11, the hybrid model described herein consists of rules which describe probabilistic relationships between medical concepts as they appear in medical texts, according to some embodiments. In the figure, QF denotes a qualified medical feature, as may be represented in a well-accepted medical ontology. The figure also shows how any concept can be qualified, and how any concepts can have different types of relations with other such qualified concepts. Some of the relations, reflected by connecting arrows, are clinical, and would typically be added by editors, whereas other relations are semantical—and originate from another source (e.g., SNOMED, LOINC, etc.).

In some cases, a qualification may be a complex array, for example when describing a feature such as pain, its location, intensity, provoking factors, etc. In some cases, the model may also take into account sub-type relations which are part of the ontology (e.g. body structures, or subtype of diseases such as iron-deficiency-anemia being a sub-type of anemia). In still further cases, models are provided that support the different types of probabilistic rules which are described in medical literature, such as complications, symptoms, lab results, risk factors, etc. In some embodiments, each such relation may be treated differently, to create a new type of rule.

According to some embodiments, an associative medical database is provided, that is a structured DB in machine readable format. According to some embodiments, human editors proficient in the relevant healthcare content are used to facilitate the content reviews, filtering and entry into the system, optionally using a template based editor, crowd sourcing platform and mechanisms for moderation and data validation. In further embodiments, at least some of the entering of healthcare publications content is integrated into the associative medical database by automated tools, optionally in cooperation with human editors.

According to yet further examples, a crowdsourcing platform is provided, wherein the crowdsourcing platform enables multiple user data entry, optionally by content experts, to allow multiple experts to enter data into the platform. In some embodiments, such expert processed content can be peer-reviewed, ranked, challenged, edited, removed etc.

In one embodiment, an automated validation testing module/function is provided, for validating data entered by a crowdsourcing user. In some embodiments, as crowdsourcing users add data into the knowledge graph, it is necessary to validate such data in order to make sure that erroneous data is not entered. In addition to manual moderation, which is commonly used in crowdsourcing platforms, an automated validation module is herein provided. In one example, a plurality of known medical cases may be used. Each case in the set of such known medical cases may include a set of findings describing a patient along with a known condition, i.e. diagnosis result. When running the diagnosis algorithm which relies on the knowledge graph and the given set of findings, the known condition should come up as the top diagnosis result. When new rules are added to the knowledge graph, the results provided by the algorithm may change. In some cases, when the algorithm fails to come up with the expected known results, the newly added data used may be flagged, such that manual moderation may be used to find discrepancies.

According to some embodiments, probabilistic associations between diseases and complications may be derived using outputs from the system, optionally generating existing and/or new associations based on the conditions being analyzed.

In some examples, certain associations are described in the medical literature, whereas the system or platform may also provide inferred associations, by analyzing the path(s) by which such associations are generated. In one example, MI is associated with Cardiomegaly, but its also associated with Hypokalemia, therefore an inferred relation may exist between Cardiomegaly and Hypokalemia, as can be seen in FIG. 10 above.

According to some embodiments, medical treatment costs, medical procedure workflows and more can be mapped, tracked and enhanced by the system, platform and methods described herein. In one example, diagnostic and/or treatment decisions may be made more effectively by instructing the system to output multiple viable treatment procedures (e.g., showing cheaper, faster or qualitative tests or procedure pathways) at a specific junction or in a specific situation, for example, prior to a more expensive or more risky pathway.

According to some embodiments, citation references may be ranked and/or scored, to indicate the strength of probabilistic rules inferred from the knowledge base. In some cases, scores relating to citation relevance, quality, etc. are entered along with the citation. In some cases, platform algorithms may provide higher scores with higher impact on associations based on a citation's ranking.

According to some embodiments, clinical findings may be entered into the platform with a list of suspected diseases (i.e. differential diagnosis), such that the platform algorithm is enabled to look up all the association for a specific disease as derived from the literature (both directly and indirectly), and be able to view the path to the original citation.

In one example, multiple pathways may be searched for when looking up Pneumonia. The system may subsequently show all associations with findings, lab tests, etc. In this example, indirect connection to other conditions may be shown, such as Edema, and for this path provided, the original citations may be read, searched, or otherwise accessed.

Medical professionals generally rely on reference apps and dedicated search engines to pull up textual medical knowledge (e.g., UpToDate or PubMed). According to some embodiments, the platform enables provision of patient-tailored reference lookup incorporated with "path-to-evidence" citations, findings and suspected diseases. Further, the system may use a differential diagnosis list as a gateway for lookup of a specific disease. In this way, without having to read text references, the platform is adapted to show all or a selected level of associations known in the literature for this disease, both direct and in-direct. Further, in the case where a clinical reason or explanation is available, for example that explains the path-to-evidence for indirect, inferred associations, the reader can be redirected to the original citation(s).

Typical diagnostic processes in clinical settings are demanding and time consuming, and often inaccurate. Typically, a doctor wanting to research for support materials is required to search for a specific concept, read large amounts of non-personalized texts or materials, and apply lessons learned to situations, if relevant.

According to some embodiments, the system described herein may provide medical knowledge that is beyond the "simulation of intelligent human behavior by machines". In some embodiments, the platform is able to simulate human type behavior by enabling access to unlimited amounts of clinical facts combined with the processing of complex probabilistic associations.

Generally, ontology sources cover only the semantic relations between medical knowledge. According to some embodiments of the present invention, the platform processes the necessary language that enables a semantic description of clinical knowledge as it appears in medical texts. Medical texts or sources can be very complex, including large number of relations between concepts. In most cases, a large number of published medical texts (e.g. chapters in a book, presentations, papers or articles etc.) are required to cover complex associations between diseases and findings. For example, in a situation such as A>B>C>D>E, where A is originating disease, and B, C, D are all disorders or complications, and E is a finding caused by complication D.

According to some embodiments, a healthcare diagnostics and treatment platform in provided, comprising a computerized model that runs on a database for storage of medical hybrid knowledge graph, a diagnostic algorithm or software which gets inputs from the hybrid knowledge graph and from given sets of patient findings or test results data, and wherein the data inputs are processed to create a list of differential diagnosis with suspected disorders, optionally with suggested next steps. Further, the platform may include frontend applications for editing, data entry, knowledge graph access and presentation of data or diagnosis results.

In some embodiments, the platform enables the translation of medical knowledge from multiple sources (e.g., books, articles, personal knowledge, test results etc.), into a hybrid knowledge graph which integrates clinical knowledge along with one or more ontology based knowledge graphs, such as SNOMED, LOINC etc. Furthermore, the knowledge graph may also integrate data of other types or from other healthcare related databases, for example data sources including costs of treatments or procedures, risks of treatments or procedures, timing of lab and imaging tests, side effects of medicines, procedures or treatments, disease prevalence and incidence rates, etc. In this way, the platform is enables to generate descriptions, diagnoses, treatment pathways etc. for patients, based on multiple medical knowledge sources, in a hybrid knowledge graph.

In some embodiments, the platform described herein includes a frontend application to enable queries into the hybrid knowledge graph and provide comprehensive presentations relating to clinical questions. A query can be as simple as retrieving all data known for a single clinical concept, or involve the input of several findings, wherein a diagnostic algorithm can be run to provide a list of differential diagnosis, for example to distinguish a particular disease or condition from others that present similar clinical features, and/or suggested next steps.

In some embodiments, the platform described herein includes a data curation module, to enable the entry, editing, reviewing etc. of healthcare data from multiple-sources into a structured database, for example, using crowdsourcing. In some embodiments, a curation mechanism may include using a templates based editor supporting data entry. Such templates are designed to support different types of clinical facts e.g. etiological, demographic, causal relations between disorders, findings and complications, risk factors, etc. The platform may enable manual moderation by community members and/or automated tools for data validation. In some embodiments, data or content validation is achieved by using the database along with a diagnostic algorithm for diagnosing a large number of known medical cases. In some cases, automated validation may be conducted on new data to make sure that diagnosis results are not impaired by adding this new data. If impaired, a flag may be raised for notifying a supervisor to conduct a manual inspection.

In some embodiments, the platform described herein includes a citation reference module, to enable the provision of source citation references for each data item in the database. In some embodiments, when diagnosis is done or other data is presented, the "path-to-citation" can be tracked and provided to the users for reference or validation purposes.

In some embodiments, the citation module includes a mechanism for ranking of citations, in order to give them weight, according to various parameters, for example, type of citation (exact or estimate), reputation of publication, reputation of source authors, etc. The platform database may include several citations addressing the same clinical information, wherein the citation module may facilitate providing each citation with its own score. A scoring algorithm, according to some embodiments, in designed to provide different weight to citations based on their scores, thereby making the relevant citations more effective as input for diagnosis algorithms, treatment algorithms etc. In one example, the platform's diagnostic algorithm may use the citation score or rank into account when calculating the probabilistic value for each such citation.

According to some embodiments, a medical practitioner user application is provided, the application running code to provide an interface to interact with the healthcare system or platform, to enable the medical practitioner to manage a patient diagnosis process.

According to some embodiments, a medical practitioner user application is provided, the application running code to provide an interface to interact with the healthcare system or platform, to enable the medical practitioner to manage a patient treatment process.

According to some embodiments, a healthcare provider end user application is provided, the application running code to provide an interface to interact with the healthcare system or platform, to enable the healthcare provider to manage diagnostic and/or treatment processes for multiple users.

According to some embodiments, an end user application is provided, the application running code to provide an interface to interact with the healthcare system or platform, to enable the end user to manage a treatment pathway.

In some embodiments, the platform described herein includes artificial intelligence (AI) algorithms that are adapted to be run on big data sets from healthcare knowledge bases, to provide enhanced medical diagnostics, treatment plans and payment plans. For example, AI and machine learning algorithms can be applied to large sets of individual patient records to look for patterns and create "clinical rules derived from big data" Such rules could be added to the hybrid knowledge graph.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A method, comprising:
diagnosing, by at least one processor, a patient with a disease from a set of suspected diseases by:
transmitting, by the at least one processor, a medical knowledge graph to a user, the medical knowledge graph depicting a plurality of nodes and a plurality of connectors between the plurality of nodes, a subset of nodes in the plurality of nodes representing a plurality of diseases and the plurality of connectors representing linkages between the plurality of nodes that are derived from (i) a plurality of ontological relationships between a plurality of medical terms comprising the plurality of diseases, and (ii) a plurality of clinical relationships between the plurality of medical terms;
defining, by the at least one processor, one or more pathways on the medical knowledge graph, the one or more pathways made by selecting connectors that connect each pair of nodes in the plurality of nodes;
determining, by the at least one processor, connection strengths between each pair of nodes in the plurality of nodes, wherein each connection strength comprises a pathway in the one or more pathways;
calculating, by the at least one processor, a total connection strength between each pair of nodes by aggregating the connection strengths;
transmitting, by the at least one processor, a graphical user interface (GUI) to receive health data from the patient;
receiving, by the at least one process, the health data;
evaluating, by the at least one processor, the health data to determine a set of nodes in the plurality of nodes that represents the health data;
determining, by the at least one processor, a set of connection strengths between (i) specific nodes in the subset of nodes representing each suspected disease in the set of suspected diseases and (ii) the set of nodes representing the health data, by using the total connection strength between each pair of nodes;
generating, by the at least one processor, a statistical correlation between each suspected disease in the set of suspected diseases and the patient health data using the set of connection strengths;

ranking, by the at least one processor, the statistical correlations;

transmitting, by the at least one processor, the statistical correlations as a list of differential diagnoses for the patient, the list comprising the set of suspected diseases and the disease having the highest statistical correlation in the statistical correlations, thereby diagnosing the disease from the set of suspected diseases, wherein the plurality of medical terms are collected from a first database, wherein the plurality of ontological relationships are collected from a second database, and wherein the plurality of clinical relationships are collected from a plurality of literature sources.

2. The method of claim 1, further comprising:

selecting a subset of pathways between each pair of nodes; and aggregating a contribution from each pathway in the subset of pathways to represent the connection strength between each pair of nodes.

3. The method of claim 2, further comprising:

transmitting a strength score indicative of reliability for each source in the plurality of literature sources.

4. The method of claim 3, further comprising:

obtaining a reputation of a publication in which each source in the one or more literature sources appears;

obtaining a reputation of one or more authors of each source in the one or more literature sources; and weighting the reputation of the publication and the reputation of the one or more authors, to generate the strength score.

5. The method of claim 1, wherein the list of differential diagnoses further comprises:

one or more disease features for each disease in the set of suspected diseases, and a likelihood that each of the one or more disease features is indicative of one or more diseases in the set of suspected diseases.

6. The method of claim 5, further comprising:

generating a first set of rules that links a specific disease in the plurality of diseases with one or more features;

generating a second set of rules that link the one or more features with one or more additional diseases other than the specific disease;

calculating a plurality of probabilistic associations between the plurality of medical conditions, the one or more disease features, and the patient health data; and weighting each probabilistic association in the plurality of probabilistic associations, to generate the likelihood.

7. The method of claim 1, wherein the plurality of medical terms additionally comprises a plurality of symptoms, and wherein the plurality of clinical relationships comprises a plurality of probabilities that individuals having a given disease in the plurality of diseases will exhibit a given symptom in the plurality of symptoms.

8. The method of claim 1, wherein the plurality of connectors comprises:

disease causes and disease types.

9. A method comprising:

transmitting, by at least one processor, a medical knowledge graph to a user, the medical knowledge graph containing a plurality of medical terms, the plurality of medical terms comprising a plurality of diseases, a plurality of conditions associated with the plurality of diseases, a plurality of symptoms associated with the plurality of diseases and the plurality of associated conditions, a plurality of complications, a plurality of laboratory tests for testing for the plurality of diseases and the plurality of associated conditions, and a conditions, plurality of treatments for treating the plurality of diseases and the plurality of associated conditions, depicting a plurality of nodes and a plurality of connectors connecting the plurality of nodes, the plurality of nodes comprising:

a first set of nodes representing the plurality of diseases, a second set of nodes representing the plurality of associated conditions, a third set of nodes representing the plurality of symptoms, a fourth set of nodes representing the plurality of complications, a fifth set of nodes representing the plurality of laboratory tests, a sixth set of nodes representing the plurality of treatments, the plurality of connectors representing linkages between the plurality of nodes that are derived from (i) a plurality of ontological relationships between the plurality of medical terms, and (ii) a plurality of clinical relationships between the plurality of medical terms, the plurality of connectors comprising:

a plurality of one-sided arrows, each of the plurality of one-sided arrows representing a causal relationship, a plurality of two-sided arrows, each of the plurality of two-sided arrows representing a clinical association;

receiving, by the at least one processor, health data associated with a patient;

selecting, by the at least one processor, one or more pathways between each pair of nodes by selecting one or more connectors that connect the pair of nodes, the one or more pathways representing one or more aspects of the patient's health data;

determining, by the at least one processor, a connection strength for each pathway between each pair of nodes;

aggregating, by the at least one processor, each connection strength to obtain a total connection strength;

generating, by the at least one processor, a statistical correlation between each disease in the one or more nodes and the patient's health data;

ranking, by the at least one processor, the statistical correlations;

generating, by the at least one processor, a list of differential diagnoses for the patient, the list of differential diagnoses comprising each disease in the one or more nodes and the statistical correlations;

transmitting, by the at least one processor, the list of differential diagnoses to the user, and diagnosing, by the at least one processor, the patient with a disease from the list of differential diagnoses that is consistent with the patient's health data.

10. The method of claim 9, wherein a probabilistic value associated with at least one of the plurality of one-sided arrows is displayed.

11. The method of claim 10, wherein the one or more pathways comprises at least one node from the fifth set of nodes and at least one node from the sixth set of nodes, and wherein the method further comprises:

determining, by the at least one processor and from the one or more pathways, a specific laboratory test in the plurality of laboratory tests to be administered to the patient; and determining, by the at least one processor and from the one or more pathways, a specific treatment in the plurality of treatments to be administered to the patient.

12. The method of claim 11, wherein the medical knowledge graph further comprises one or more literature source citations displayed in association with the one or more pathways, wherein the one or more literature source citations provide additional information relating to at least one of: one or more nodes in the one or more pathways, and one or more connectors in the one or more pathways.

13. A method comprising:
   transmitting, by at least one processor, a graphical user interface (GUI) configured to permit a healthcare practitioner to enter health data associated with a patient;
   transmitting, by the at least one processor, a medical knowledge graph depicting a plurality of nodes and a plurality of connectors connecting the plurality of nodes, wherein:
      a first set of nodes in the plurality of nodes represents a plurality of diseases,
      a second set of nodes in the plurality of nodes represents a plurality of conditions associated with the plurality of diseases,
      a third set of nodes in the plurality of nodes represents a plurality of symptoms associated with the plurality of diseases and the plurality of associated conditions,
      a fourth set of nodes in the plurality of nodes represents a plurality of complications associated with the plurality of diseases and the plurality of associated conditions,
      a fifth set of nodes in the plurality of nodes represents a plurality of laboratory tests for testing for the plurality of diseases and the plurality of associated conditions,
      a sixth set of nodes in the plurality of nodes represents a plurality of treatments for treating the plurality of diseases and the plurality of conditions,
      the plurality of connectors comprises arrows denoting probabilistic linkages between nodes in the plurality of nodes;
   receiving, by the at least one processor, the patient's health data;
   selecting, by the at least one processor, one or more pathways between each pair of nodes by selecting one or more connectors that connect the pair of nodes, the one or more pathways representing one or more aspects of the patient's health data;
   transmitting, by the at least one processor, the one or more pathways;
   determining, by the at least one processor, an aggregated connection strength for each of the one or more pathways, wherein the aggregated connection strength is determined based on the probabilistic linkages;
   generating, by the at least one processor, a statistical correlation between each disease in the one or more pathways and the patient's health data;
   ranking, by the at least one processor, the statistical correlations;
   generating, by the at least one processor, a list of differential diagnoses for the patient, the list of differential diagnoses comprising each disease in the one or more pathways and the statistical correlations;
   diagnosing, by the at least one processor, the patient with a disease from the list of differential diagnoses; and
   transmitting, by the at least one processor, to the user both the list of differential diagnoses and the disease.

14. The method of claim 13, further comprising:
   determining, by the at least one processor and from the one or more pathways, a specific laboratory test in the plurality of laboratory tests to be administered to the patient; and
   determining, by the at least one processor and from the one or more pathways, a specific treatment in the plurality of treatments to be administered to the patient,
   wherein the medical knowledge graph further comprises a cost of the specific laboratory test and a cost of the specific treatment.

* * * * *